United States Patent [19]
Levitan

[11] Patent Number: 5,973,728
[45] Date of Patent: Oct. 26, 1999

[54] DIRECT LARYNGOSCOPY VIDEO SYSTEM

[75] Inventor: Richard M. Levitan, New York, N.Y.

[73] Assignee: Airway Cam Technologies, Inc., Radnor, Pa.

[21] Appl. No.: 08/576,575

[22] Filed: Dec. 21, 1995

Related U.S. Application Data

[63] Continuation-in-part of application No. 08/240,003, May 9, 1994, abandoned.

[51] Int. Cl.$^6$ ............................... H04N 7/18; A61B 1/04
[52] U.S. Cl. .......................... 348/77; 348/376; 600/189
[58] Field of Search .................................. 348/61, 63, 64, 348/77, 78, 79, 80, 373, 376, 211; 600/188, 189, 111, 166; 345/8

[56] References Cited

U.S. PATENT DOCUMENTS

| | | | |
|---|---|---|---|
| 3,236,578 | 2/1966 | Mackworth | 351/7 |
| 3,919,475 | 11/1975 | Dukich et al. | 178/7.91 |
| 4,051,534 | 9/1977 | Dukich et al. | 348/211 |
| 4,398,799 | 8/1983 | Swift | 350/174 |
| 4,516,157 | 5/1985 | Campbell | 358/108 |
| 4,616,257 | 10/1986 | Kloots et al. | 358/93 |
| 4,621,283 | 11/1986 | Feinbloom | 358/93 |
| 4,722,601 | 2/1988 | McFarlane | 345/8 |
| 4,797,736 | 1/1989 | Kloots et al. | 348/77 |
| 4,970,589 | 11/1990 | Hanson | 358/108 |

OTHER PUBLICATIONS

Anesthesia, Third Edition, RD Miller, editor, p. 1271 Churchill Livingstone, New York, 1990.

Morales, GA, Gilbert, TB. An Aid for Simultaneous Instructor and Trainee Viewing of Orotracheal Intubation, Anesthesiology 74: 1173–1174, 1991.

Primary Examiner—Amelia Au

[57] ABSTRACT

A miniature video camera (18) mounted on a pair of goggles (12) that substantially captures the monocular perspective of the operator's right eye during the medical procedure of direct laryngoscopy and tracheal intubation. The camera is connected to a pentaprism (14) that the operator aligns with the area of interest by slight changes in head position and reference to alignment bands (46) alongside the prism body. The image is reflected through the pentaprism to the camera and then displayed on a nearby video monitor (38). Auxiliary light sources or specialized equipment are not required. Persons other than the laryngoscopist can see the procedure as it is being performed. The pentaprism, camera, and camera mount do not significantly interfere with the operator's vision or performance of direct laryngoscopy or other procedures.

14 Claims, 6 Drawing Sheets

DIRECT LARYNGOSCOPY VIDEO SYSTEM

This is a continuation-in-part of application Ser. No. 08/240,003 filed on May 9, 1994, now abandoned.

Background—Field of the Invention

This invention relates to medical imaging, specifically to head mounted video cameras designed to image medical procedures.

Background—Discussion of Prior Art

Direct laryngoscopy and intubation of the trachea is a difficult medical procedure to teach, supervise, and photograph. The larynx is located deep in the throat and the operator must displace the jaw, tongue and epiglottis with a laryngoscope in order to see the vocal cords. The oral, laryngeal, and pharyngeal axes must be properly aligned in order to visualize the glottic opening [see R. D. Miller, *Anesthesia*, 3rd Edition, Page 1271, Churchill Livingstone, New York, 1990]. Because of the limited opening of the mouth and the restrictions of the teeth and tongue the operator is essentially looking down a narrow tube. The visual restrictions of this tubular structure force the laryngoscopist to rely on monocular vision when viewing the glottic opening or vocal cords. The parallax view from the other eye is too different to see the vocal cords. The laryngoscopist's head obstructs the view of anyone else who tries to see down to the vocal cords at the same time as the laryngoscopist. Consequently, a teacher or supervisor standing behind or beside the laryngoscopist cannot visualize the most critical component of the procedure.

It is essential that the endotracheal tube is placed correctly between the vocal cords and into the trachea. Posterior to the vocal cords is the esophagus. Unrecognized endoesophageal intubation will result in death if the patient is not able to breath on his own.

There is one reference in the literature that specifically addresses the problem of supervising direct laryngoscopy. It is found in the journal *Anesthesiology* from Jun. 1991 [Volume 74, (6) 1173–4]. Entitled "An Aid for Simultaneous Instructor and Trainee Viewing of Direct Orotracheal Intubation," the letter describes modification of a standard laryngoscope blade so a fiberoptic scope can be easily attached. The letter begins:

"Tracheal intubation is among the most important techniques that anesthesia trainees learn during graduate medical education. Yet anyone who has attempted to teach this skill and to view laryngoscopy from a distance (e.g. over the shoulder) knows how difficult it is to confirm just exactly what the student is visualizing. We report a simple modification of readily available tools that will assist those teaching laryngoscopy and tracheal intubation while affording a continuous and direct view of the procedure."

Their system involves modifying a standard laryngoscope blade so a fiberoptic scope can be attached. This solution, however, does not provide the perspective of the laryngoscopist because the camera perspective is from within the oral cavity. Additionally, vomitus and blood in the airway will obscure the tip of the fiberoptic scope. Furthermore, the scope must be resterilized after each use because it is inserted into the patient's oral cavity.

Numerous devices have been invented to improve the laryngoscopist's view of the vocal cords for the purpose of endotracheal intubation. There are hundreds of different designs for laryngoscope blades. Changing the blade shape does not affect the fundamental physical restrictions which prevent others from being able to view the procedure, however. There are also numerous fiberoptic devices for viewing the larynx, such as fiberoptic laryngoscopes and flexible fiberoptic bronchoscopes. These devices are all inserted into the oropharynx. The tip of the fiberoptic elements must be positioned very close to the structures of interest because of the very limited focal distance inherent to this technology. By being so close to the structures of interest these devices obtain photographs and video images of the larynx far superior to any that could be obtained from outside the oropharynx. In fact, their design obviates the need for displacing the jaw, tongue and epiglottis as is done during standard direct laryngoscopy. The drawback of these devices, however, is that they cannot be used to teach, supervise or record direct laryngoscopy as seen by the laryngoscopist because they all view the larynx from a position deep within the oral cavity. Additionally, these devices must be resterilized between each patient contact because they enter the oral cavity. When blood and other secretions are present these devices perform poorly because the fiberoptic lens surface is covered.

There is extensive prior art on cameras mounted on headsets for videotaping surgical and other procedures. N. H. Mackworth et. al., U.S. Pat. No. 3,236,578 issued Feb. 22, 1966, described a head mounted camera for the purpose of determining the point of visual concentration of a subject. The camera lens on this device is located on top of the subject's head. Dukich et. al., U.S. Pat. No. 3,919,475 issued Nov. 11, 1975, describes a head attached television for use in displaying and recording surgical procedures. In this design a mirror mounted on the forehead is used to reflect an image to a camera positioned on the top of the head. Another example of a head mounted television camera is by J. Kloots, U.S. Pat. No. 4,616,257 issued Oct. 7, 1986. In this invention a camera and illuminating system mounted on a headset are positioned between the user's eyes. Similar to this invention is U.S. Pat. No. 4,621,283 issued Nov. 4, 1986 to R. Feinbloom. This design uses a mirror mounted just over the nasal bridge to reflect an image from the surgical field to the head mounted camera. These and other head mounted cameras designed for surgeons will not work for recording direct laryngoscopy. Even though they have camera views that eventually converge with the surgeon's view the parallax is too significant over the shorter focal distance involved in direct laryngoscopy. The camera position in all these systems will not provide for visualization of the vocal cords.

Because of the visual restrictions inherent to laryngoscopy there can be virtually, no vertical discrepancy between the camera's perspective and the eye used to visualize the vocal cords. This vertical restriction is imposed by the need to align the oropharyngeal, pharyngeal, and laryngeal axes in order to expose the vocal cords to direct view. If a camera is mounted above or below the operator's line of sight the camera's view of the vocal cords will be obscured by the patient's lips, teeth, or epiglottis, or by laryngoscope blade.

The right eye is primarily used to visualize the cords because right eye dominance, like right handedness, is much more common. Additionally, the mechanics of the procedure itself force the use of the right eye when sighting the vocal cords. This is due to laryngoscope blade design. All laryngoscopes are designed to be held in the left hand. Laryngoscope blades have a flange along the left side of the blade to help sweep the tongue towards the left side of the mouth during the procedure. Because of this flange and the resultant presence of the tongue on the left side of the mouth the operator must look down the center and right side of the mouth to see the vocal cords. For this reason the endotracheal tube is held by the right hand and is passed down the right side of the mouth into the glottic opening.

The visual restrictions as described above impose strict limits on any camera system designed for imaging direct laryngoscopy. The camera's perspective must be vertically aligned with both the operator's line of sight and the alignment of the oropharyngeal, pharyngeal, and laryngeal axes. Furthermore, the camera's perspective must be horizontally aligned with the right eye or immediately lateral to the right eye.

All examples of prior art fail to meet both of these essential requirements. Cameras which capture a perspective from the forehead or nasal bridge will not be vertically aligned in a manner that will allow visualization of the cords. Instead, the camera's perspective will be blocked by the upper teeth, the upper lip, the epiglottis or the laryngoscope. Cameras mounted midway between the eyes have a three or four centimeter horizontal discrepancy between the camera's view and the view of the right eye. The camera's view in these systems will be blocked by the tongue or the laryngoscope blade when the right eye is visualizing the vocal cords.

Most significantly, all examples in the prior art have a camera orientation dictated only by the direction of the head. There is no means of aligning the sight of the operator and the camera's view other than by referring to the video monitor. When the surgeon's head is pointing downwards the camera will capture that image even if his eyes are directed upward. This is not a problem during surgery since there is little movement of the surgeon's head and the field of interest stays in relatively the same position. Direct laryngoscopy, in contrast, is a dynamic procedure. The field of interest and the operator are moving simultaneously. At the start of laryngoscopy the operator is looking down at the mouth from above the patient. As the laryngoscope is inserted into the mouth the head of the operator is brought lower and his line of vision angled upwards. Simultaneously, the patient's head and jaw is manipulated through traction on the laryngoscope in order to expose the vocal cords to direct view.

In terms of time, surgical procedures occur over the course of hours. Camera orientation, focus, and magnification can be checked on the monitor and adjustments made as needed. Direct laryngoscopy and intubation usually occur within ten seconds and should never exceed 30 seconds. The laryngoscopist cannot look away from the vocal cords during the procedure. There is no time to refer to the video monitor. There is no time to adjust the camera's focus or orientation.

Following intubation the laryngoscopist has multiple tasks to perform immediately. The breathing tube must be connected to a ventilation apparatus, a quick physical exam of the lungs must be done, and multiple monitors and instruments must be checked and adjusted. These include the ventilator, the anesthesia machine, and monitors that display vital signs and exhaled gases. Therefore, the operator must be able to look quickly in many different places without having a bulky camera mount or related piece of equipment obstructing the view. The prior designs of head mounted televisions for surgeons fail to meet this requirement as well.

The inadequacy of surgical imaging systems for imaging direct laryngoscopy is further evident by the complete lack of application for this purpose. This is despite the commonplace presence of these imaging systems in the operating rooms at major teaching institutions.

Other examples of head and goggle mounted television cameras are found in several non-medical inventions. A portable electronic camera by M. Campbell, Pat. No. U.S. 4,516,157 issued May 7, 1985 incorporates a video recording device into a pair of spectacles. The camera in this invention is positioned on either the nasal bridge or the temples. Like the surgical devices the discrepancy between the right eye and the camera is too far for use in direct laryngoscopy. Similar to the surgical cameras the orientation of this device is dependent on how the spectacles ride on the head and which way the head is directed. Further examples of spectacle and head mounted cameras are shown in head-up displays designed for pilots and soldiers. D. Swift, U.S. Pat. No. 4,398,799 issued Aug. 16, 1983, entails a head up display system that incorporates a helmet mounted camera. The camera view is obtained from the nasal bridge and is dependent on the orientation of the head. Further refinements of a head mounted video camera and display are in U.S. Pat. No. 4,970,589 by C. M. Hanson, issued Nov. 13, 1990. Though this invention primarily concerns a weapon mounted video camera, further embodiments of the invention depict the camera being mounted on goggles. As evident by the various designs and intended uses this system is designed for very long focal distances which are required when sighting targets on a battlefield. The camera's perspective is from either the nose bridge or forehead. This type of camera mount designed to capture a binocular perspective will not work for direct laryngoscopy for the reasons cited above.

Objects and Advantages

By means of the present invention the problems associated with displaying and recording the procedure of direct laryngoscopy and intubation are solved. Among the objects and advantages of the invention is that the camera image obtained during laryngoscopy is nearly identical to the monocular perspective from the laryngoscopist's right eye. Through an alignment means the operator can ensure that the camera will visualize the target without having to verify this on a video monitor. An essential object of the invention is that it does not interfere with performance of intubation and other procedures that must be performed prior to and immediately following intubation. It is an additional object of the invention that different persons can correctly use the device with minimal or no adjustment and minimal training. A further advantage of the invention is that the system works well with standard laryngoscopy equipment. No additional light sources or special laryngoscopes are required to obtain a good video image. Because the camera is mounted on a pair of protective goggles the laryngoscopist is protected from potential eye contact with the patient's vomitus, blood, and other secretions. The device can be used repeatedly without the need for sterilization because it never touches or enters the patient's body.

By capturing the perspective of the laryngoscopist the invention can serve as an aid for teaching, supervising, and recording the critical medical procedure of endotracheal intubation. Various interventions commonly performed during laryngoscopy to improve the laryngoscopist's view can be immediately assessed by the supervisor. Such interventions include repositioning the head, inserting and lifting on the laryngoscope handle in various ways, suctioning the secretions from the patient's mouth, and applying pressure to the cricoid cartilage to improve the laryngeal view.

Using my direct laryngoscopy video system the supervisor can verify that the student does in fact sight and correctly identify the vocal cords prior to attempted intubation of the trachea. Prior to this invention, the supervisor has been dependent on the student to report what she sees. Even if the student is truthful she may not be able to accurately report what structures are visualized because she has limited or no past experience in doing the procedure. There is significant performance anxiety on the part of students and physicians in training because of the critical nature of the procedure. If the student hesitates about what is visualized or admits that the vocal cords are not well seen then the supervisor will perform the procedure in the interest of patient safety. My invention would improve communication between student and supervisor and improve the teaching of the procedure as it is being performed.

Regarding the most critical part of the procedure, placing the endotracheal tube in the correct orifice, the supervisor and persons other than the laryngoscopist can watch as the tube is placed between the vocal cords.

The video output of my invention also allows for other junior personnel in the room to benefit educationally by witnessing what is occurring within the mouth. Traditionally there has been little educational benefit to watching someone else perform direct laryngoscopy. Using my invention the teacher or the laryngoscopist can narrate what is going on while it occurs. The students can visualize the appropriate landmarks as they come into view on the video monitor.

The direct laryngoscopy video system provides for the first time the ability to objectively record the laryngeal view obtained during direct laryngoscopy. Various parameters of airway assessment, evaluated prior to intubation, can now be correlated objectively with the laryngeal view obtained. Such parameters include the shape of the jaw, prominence of the teeth and tongue, distance from the jaw to the larynx and numerous other distances. In part because there has been no objective way to record laryngoscopic view, there is much debate over which of these parameters are most predictive of a difficult airway. My direct laryngoscopy video system would allow for such objectification and research studies and will ultimately enhance the body of knowledge and improve the safety of airway management.

Further objects and advantages of my direct laryngoscopy video system will become apparent from a consideration of the drawings and ensuing description.

Drawing Figures

Reference Numerals in Drawings 10 operator's head
12 goggles
14 prism body
16 prism face
18 camera
20 heat shrink tubing
22 camera band
24 camera mount connection
26 horizontal adjustment track
28 head band
30 cable plug to camera
32 cable
34 cable clamp
36 camera control device
38 video monitor
40 video cassette recorder
42 operator's right eye
44 line of sight from right eye to target (vocal cords)
46 alignment bands
48 angle adjustment mechanism
50 left hand of operator
52 laryngoscope handle
54 laryngoscope blade
56 base of laryngoscope blade
58 flange of laryngoscope blade
60 laryngoscope light source
62 patient's upper lip
64 patient's lower lip
66 epiglottis
68 trachea
70 esophagus
72 tongue
74 valecula
76 oral cavity
78 patient's head
80 patient's upper teeth
82 patient's lower teeth
84 vocal cords
86 glottic opening into trachea
88 corniculate cartilages
90 wing nut
92 track mounting bolts
94 angle adjustment screw
96 inner track member
98 beam splitting cube prism
100 high intensity light source Description of the Drawing FIGS. 1–9

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for claims and as a representative basis for teaching one skilled in the art to variously employ the present invention in virtually any appropriately detailed structure.

Figure 1:
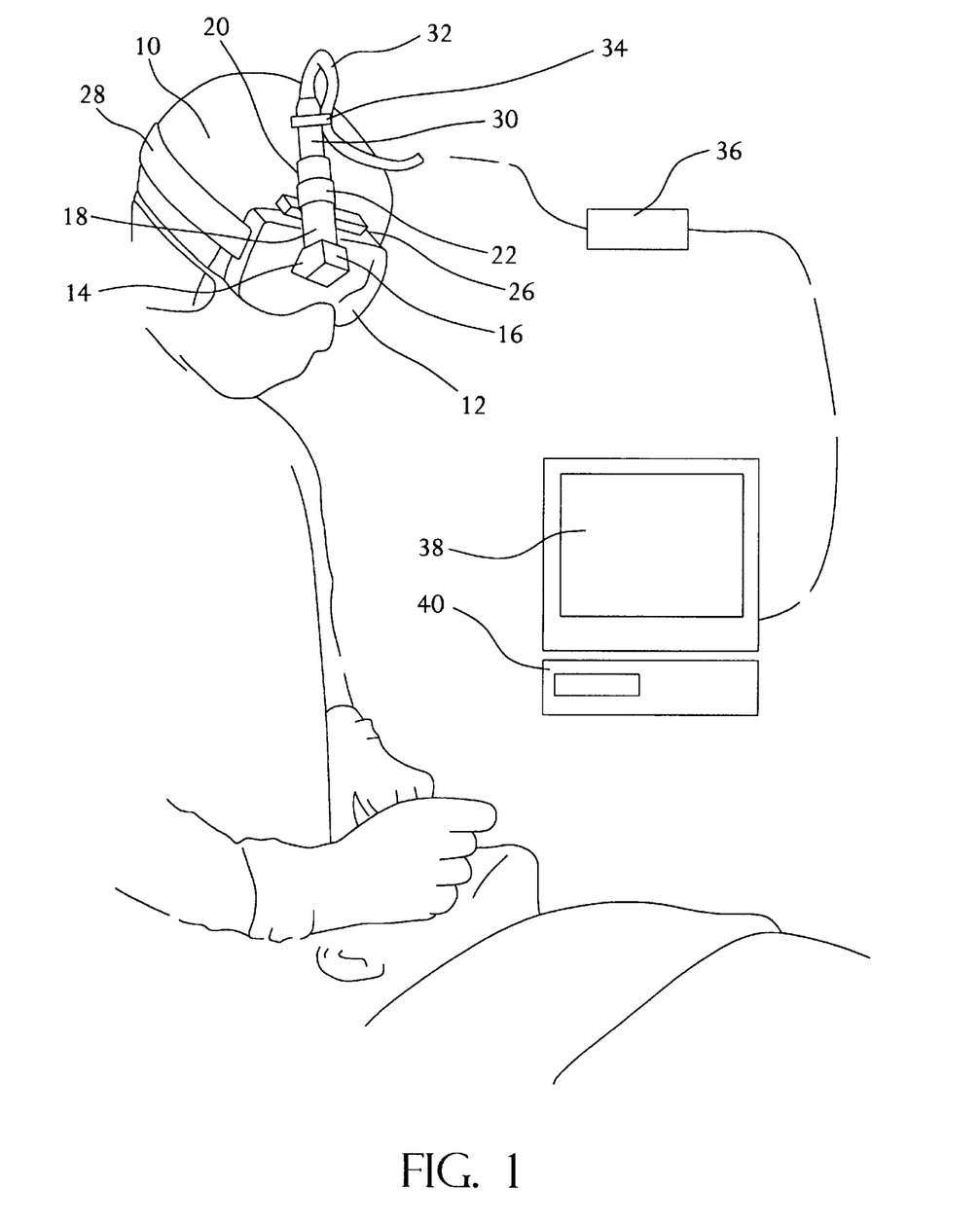
FIG. 1 shows the operator wearing the invention and providing patient care at the head of the table while looking down towards the patient.

FIG. 1 shows the operator wearing the invention and providing patient care at the head of the table while looking down towards the patient. A miniature video camera 18 is connected by a piece of heat shrink tubing 20 [seen best in FIG. 3] to a pentaprism 14. One example of such a miniature camera is produced by Panasonic Communications and Systems Company, Secaucus, N.J. Their model number GP-KS102 industrial CCD microcamera measures ⅔" diameter by 1⅞" long and can be connected to a 15 mm telephoto lens, model number GP-LM15T. Through a camera band 22 and a horizontal adjustment track 26 the camera 18 and pentaprism 14 are mounted on a pair of goggles 12. The goggles 12 are secured on an operator's head 10 with a head band 28. Coming from the camera 18 is a cable plug 30 connected to a cable 32. The cable 32 connects the camera 18 to a conventional receiving device or camera control device 36. The camera control device 36 is connected to a standard video monitor 38 and a video cassette recorder 40.

Figure 2:
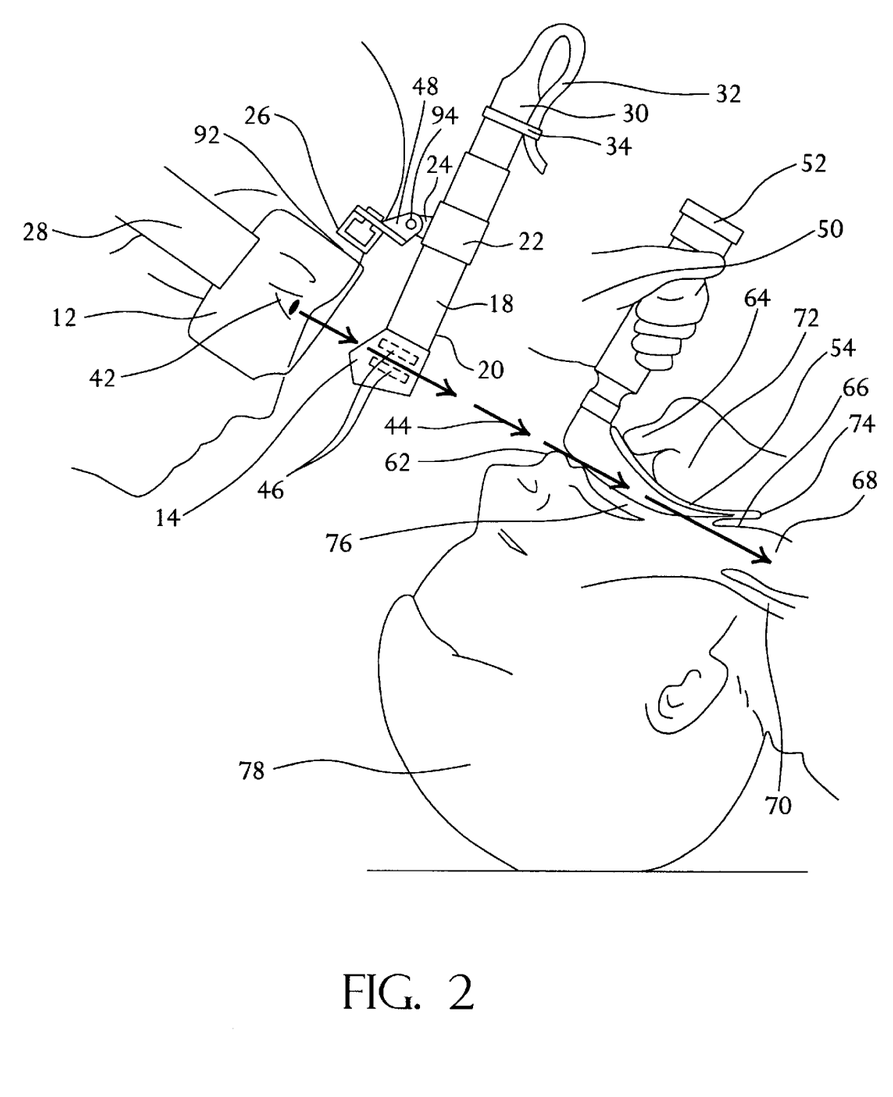
FIG. 2 shows the alignment of the operator's right eye, the prism with attached camera, and the tracheal opening during direct laryngoscopy.

FIG. 2 shows the alignment of an operator's right eye 42, the prism 14, and the trachea 68 during direct laryngoscopy. A line of sight 44 originating from the operator's right eye 42 is directed towards the trachea 68. A prism face 16 and prism body 14 have been aligned with this line of sight 44 by the operator using a colored alignment band 46. These alignment bands 46 are located on the medial aspect of the prism 14.

FIG. 2 also shows other details of this embodiment of the invention including a camera mount connection 24 which connects the camera band 22 to an angle adjustment mechanism 48 and thereby to a horizontal adjustment track 26. The angle adjustment mechanism 48 has an angle adjustment screw 94. Also shown is a track mounting bolt 92 which secures the horizontal adjustment track 26 to the goggles 12.

FIG. 2 shows additional details of direct laryngoscopy which are relevant to understanding the restricted view during this procedure. An operator's left hand 50 is applying traction to a laryngoscope handle 52 that is connected to a laryngoscope blade 54. A patient's head 78 is shown in the extended position used during laryngoscopy. The laryngoscope blade 54 has been inserted into an oral cavity 76 between an upper lip 62 and a lower lip 64 of a patient. The laryngoscope blade 54 is lifting a tongue 72 and the tip of the blade is lodged in a valecula 74. By traction on the valecula 74 the operator has displaced an epiglottis 66. This allows visualization of the opening of the trachea 68. Posterior to the trachea 68 is an esophagus 70.

Figure 3:
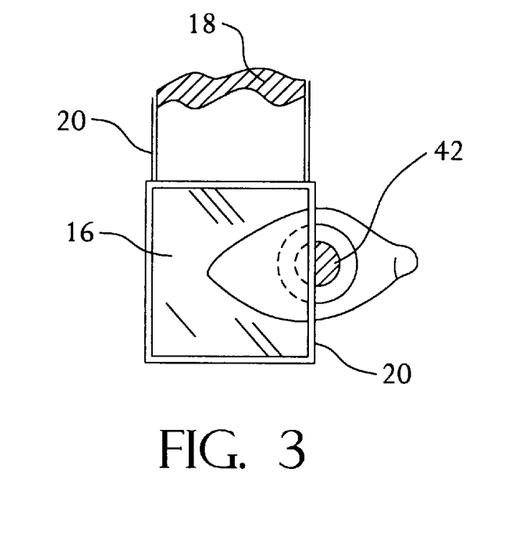
FIG. 3 shows the relationship of the prism face with the operator's right eye when the camera has been aligned with the target.

FIG. 3 shows the relationship of the prism face 16, and therefore the camera's view, with the operator's right eye 42 when the prism has been aligned with the target. The camera 18 is shown connected to the prism face 16 with section of heat shrink tubing 20.

Figure 4:
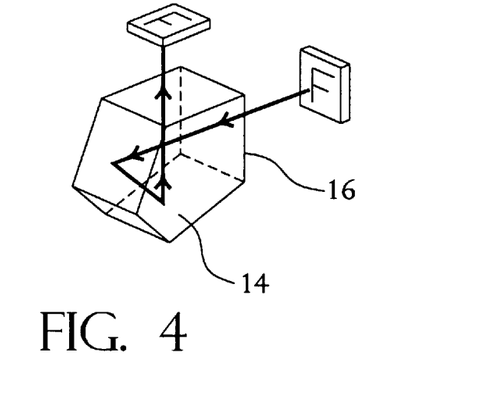
FIG. 4 shows the path of light as it is reflected from the target, represented as the letter "F," towards the camera.

FIG. 4 shows the path of light taken through the five sided pentaprism 14. After entering through the prism face 16 the light is reflected 90 degrees through two reflections. The reflecting surfaces are silvered. The image emerges from the prism and is directed towards the camera 18 [not shown in this drawing]. As evident by the letter "F" the image is right left correct and upright as it exits the prism 14.

Figure 5:
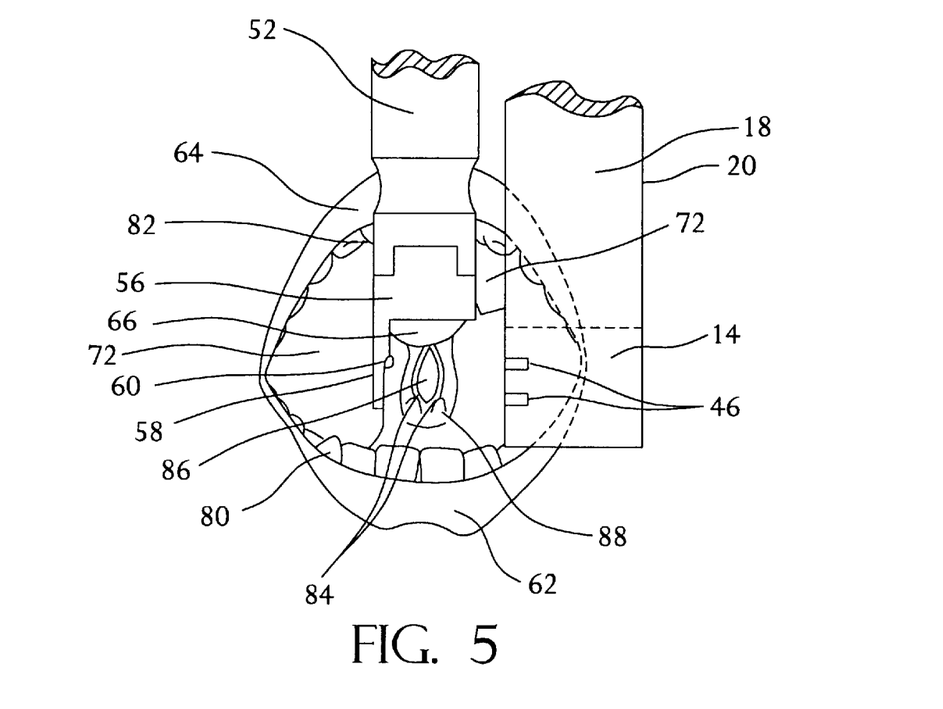
FIG. 5 shows the patient's mouth and vocal cords as seen from the operator's perspective during direct laryngoscopy.

FIG. 5 shows a pair of vocal cords 84 and other intraoral landmarks as visualized by the operator during direct laryngoscopy. In the foreground on the right side of the drawing is the camera 18 and the prism 14 as seen posteriorly from the operator's perspective. A base of a laryngoscope blade 56 and a flange of a laryngoscope blade 58 are shown in the patient's mouth from the perspective of the operator. The laryngoscope handle 52 is held by the operator's left hand [not shown]. The flange of the laryngoscope blade 58 has been used to sweep the patient's tongue 72 from right to left.

A laryngoscope light source 60 can be seen alongside the laryngoscope blade 58. This light source 60 provides illumination of the epiglottis 66, the vocal cords 84, and the glottic opening 86. The upper lip 62 and lower lip 64, and the upper and lower teeth, 80 and 82, respectively, provide boundaries to the oral cavity. The laryngoscope blade is lifted upwards along the axis of the laryngoscope handle 52 to distract the epiglottis 66. This is done by upwards traction on the valecula [not seen] where the base of the laryngoscope blade is positioned [see FIG. 2, 74]. The glottic opening 86 is the entrance into the trachea between the vocal cords 84. Posterior to the vocal cords are a pair of corniculate cartilages 88. The esophagus [not shown in this figure, see FIG. 2, 70] is beneath, i.e. posterior to the corniculate cartilages 88. The colored alignment bands 46 have been vertically aligned with the glottic opening 86. This ensures that the prism 14 is correctly directed at the target. The heat shrink tubing 20 can be seen surrounding the camera 18 and the prism 14.

Figure 6:
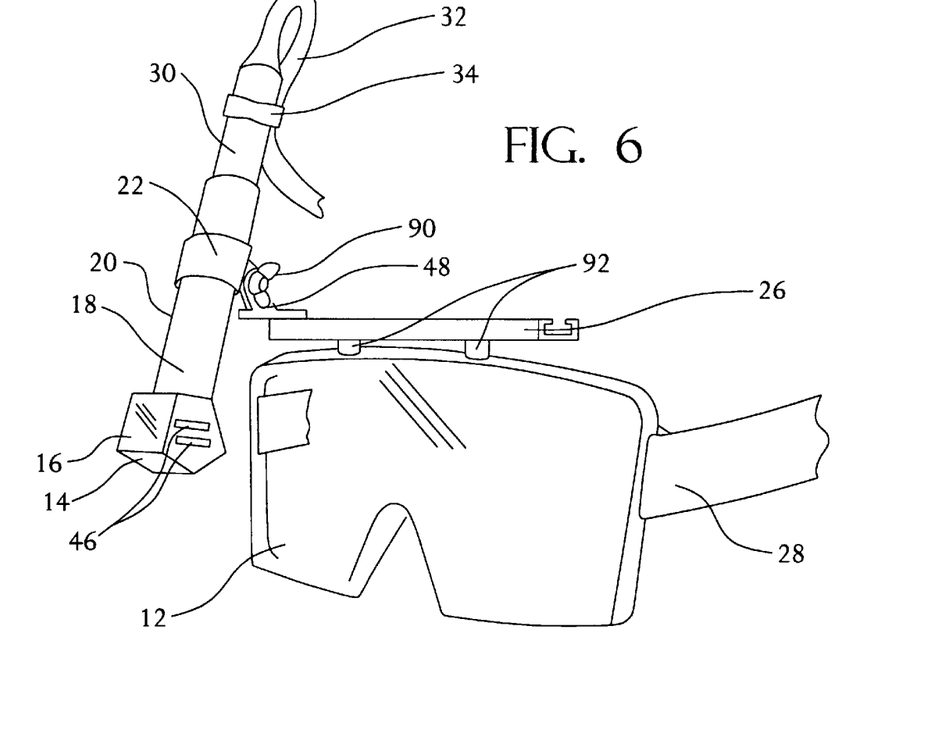
FIG. 6 shows an oblique perspective of the goggle-mounted direct laryngoscopy camera.

FIG. 6 shows an oblique perspective of this embodiment of the goggle-mounted direct laryngoscopy camera. In this view the goggles 12 are shown free standing. The head band 28 is seen coming from the goggles 12. The horizontal adjustment mechanism 26 can be seen connected to the goggles 12 by means of the track mounting bolts 92. Attached to the horizontal adjustment track 26 is the angle adjustment mechanism 48. A wing nut 90 allows for adjustment of the camera band 22 in relation to the angle adjustment mechanism 48. Loosening of the wing nut 90 releases the tension on the camera band. It also allows a camera mount connection 24 (see FIG. 7) to pivot on the angle adjustment mechanism 48. In this perspective the colored alignment bands 46 can be seen on the medial aspect of the prism 14. The prism face 16 points outward towards the area of interest. The camera band 22 grasps the camera 18 which is encased in heat shrink tubing 20. The heat shrink tubing 20 secures the prism 14 to the camera 18. At the top of the camera 18 is the cable plug 30 and cable 32. The cable 32 is held to the cable plug 30 by a cable clamp 34. The cable clamp 34 prevents undue torque on the cable plug 30 insertion into the camera 18.

Figure 7:
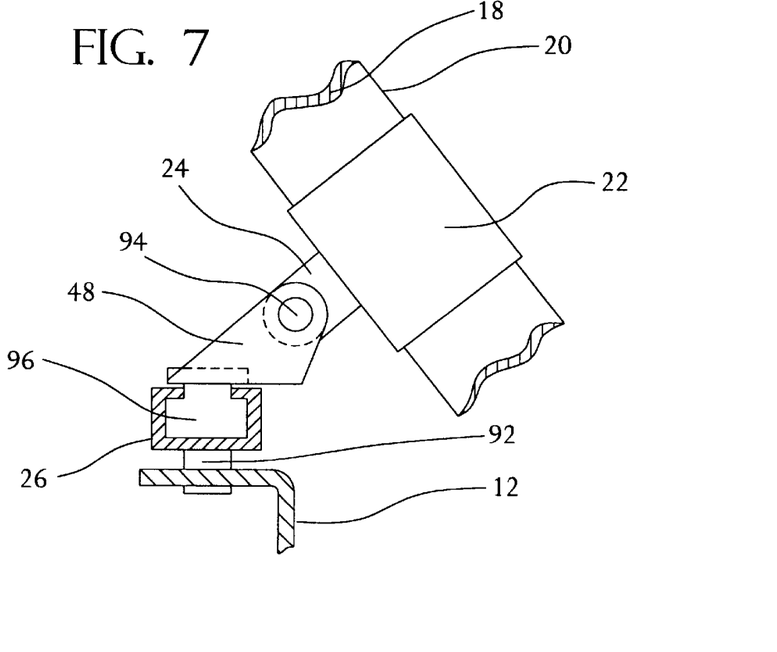
FIG. 7 shows the camera band and the angle adjustable mounting mechanism between the camera and the horizontal adjustment track.

FIG. 7 shows a side view of the horizontal adjustment track 26, the angle adjustment mechanism 48, and the camera band 22. This perspective provides a side view of the goggles 12, and their relationship to the track mounting bolts 92. It also shows the horizontal adjustment track 26 on edge with the inner track member 96. The inner track member 96 slides within the horizontal adjustment track 26 and connects to the angle adjustment mechanism 48. The angle adjustment screw 94 connects the angle adjustment mechanism 48 to the camera mount connection 24. The camera mount connection 24 connects with the camera band 22 which wraps around the heat shrink tubing 20 and the camera 18.

Figures 8, 9:
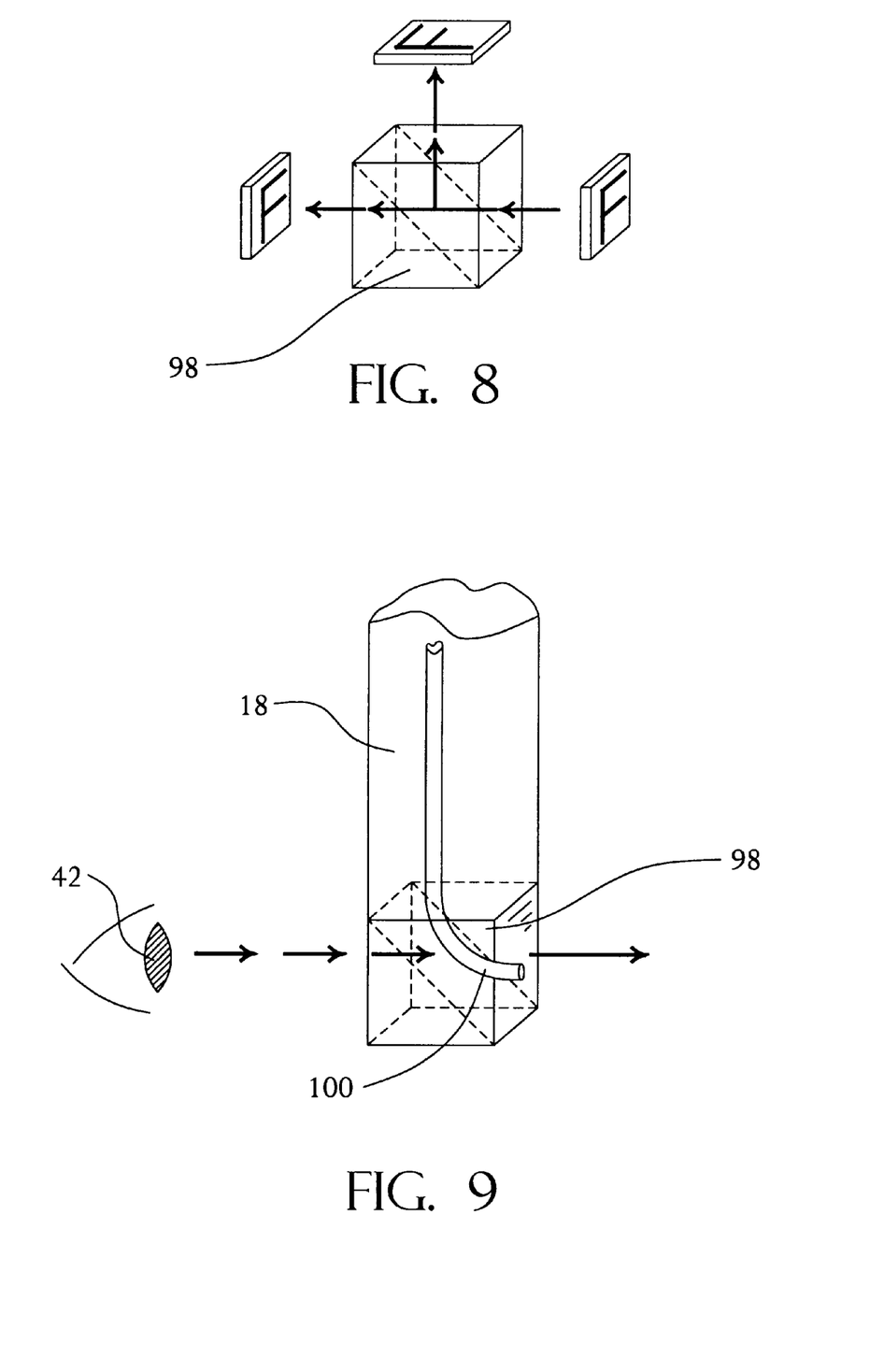
FIG. 8 shows the path of light, as represented by the letter "F," through a beam splitting cube prism.
FIG. 9 shows another embodiment of the invention with a beam splitting cube prism and an additional light source connected to the camera.

Other more complicated embodiments of the invention are possible and readily imaginable to any person skilled in the art. For example, a beam splitting cube prism 98 as shown in FIGS. 8 and 9 could be attached to the camera 18. Such a prism is sold by Edmund Scientific Company of Barrington, N.J. The operator looks directly through the prism towards the area of interest. The camera 18 receives a reflected image identical to the transmitted image seen by the operator. The operator's perspective and the camera's perspective are therefore aligned and correctly pointed to the area of interest. Because the light rays are split with some of the light going towards the camera 18 and some toward the operator's eye an additional high intensity light source 100 is required. This high intensity light is used by the operator to improve illumination of the work area and delineate the field of view seen by the camera 18. Alternatively, additional light could be provided by a high intensity light source on the laryngoscope. Laryngoscopes that use fiber optic technology to provide a light source much brighter than the standard laryngoscope bulb are already in use.

While the beam-splitter prism enables a direct line of sight through the prism, with an image reflected upwards to the camera, it requires the use of a video mirror device 99 (see FIG. 10) to flip the reflected image over and make it right-left correct. The video mirror device 99 is a separate box with a circuit board that is connected by cable between the camera box and the video monitor. Video mirror devices are well known, a preferred device being available from Colorado Video of Denver, Colo.

As video technology continues to improve it is expected that a high quality camera will be available that is smaller than the one described above. When this occurs a reflecting means will not be necessary. The camera will be small enough to placed directly in-line between the operator's right eye and the target.

Other embodiments wherein the camera is mounted on a head band or other head mounted structure are readily envisioned.

Figure 10:
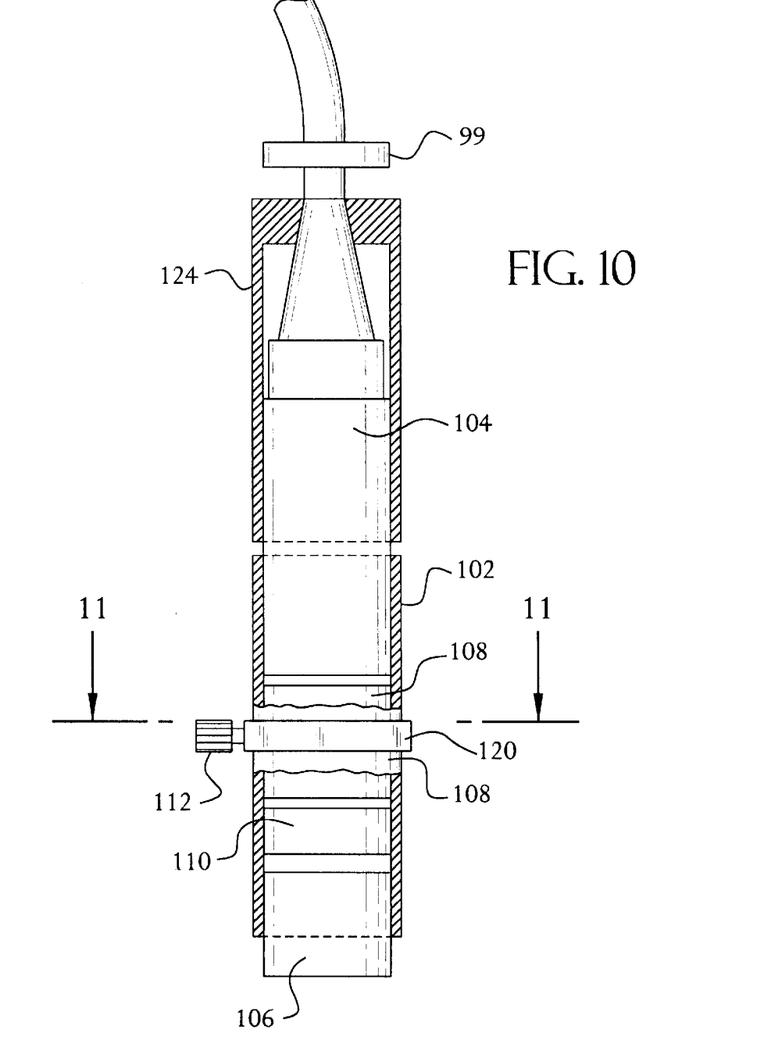
FIG. 10 is a fragmentary schematic top plan view (fragmentary) of the system of the present invention wherein a boot connects the prism to the camera body.
Figure 11:
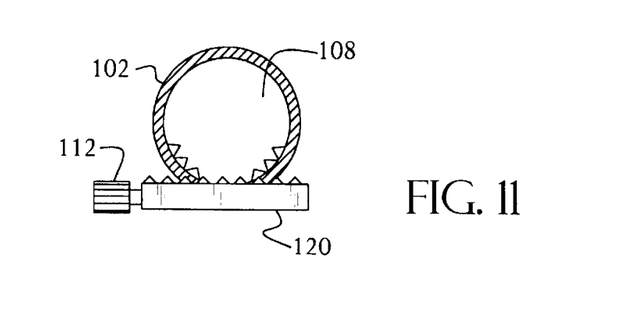
FIG. 11 is a sectional view taken along the line 11—11 of FIG. 10.

Referring now to FIG. 10, therein illustrated schematically is a device according to the present invention which enables the focal length or focus of the lens to be adjusted without removal of the prism from the camera body. More particularly, a cylindrical boot 102 is mounted at one end on the camera body 104 (e.g., by hexagonal nuts) and at the other end to the prism 106, which may be a beam splitter or pentaprism, as described above (e.g., by hex nuts). Forwardly of the camera body 104 are the lens 108 (held by a lens-holding element 109 for rotation with lens 108 as a unit) and the iris 110 (both the lens 108 and iris 110 being able to freely rotate together as a unit within the boot 102). The focus adjustment mechanism 120 enables the lens 108 to be rotated within the boot 102 relative to the camera body 104. Typically the lens-holding element 109 and the focus adjustment mechanism 120 constitute a worm gear mechanism. As best illustrated in FIG. 11, the focus adjustment mechanism 120 includes a focus adjustment screw 122 having a manually rotatable knurled head outside of the boot 102 and an externally threaded body extending through the boot 102 and engaging within the boot 102 an externally threaded outer circumference of the lens-holding element 109 such that rotation of the focus adjustment screw 112 results in rotation of the lens-holding element 109—and hence lens 108—within boot 102 relative to camera body 104, thereby changing the focal length. The iris 110 is directly secured to the lens 108 for rotation therewith as a unit and is locked in the open position so as to maximize the light passing into the lens 108. Thus, the rotation of the focus adjustment screw 112 causes the lens 108, lens-holding element 109 and iris 110 to rotate as a unit relative to the camera body 104, thereby to adjust the focal length of the lens 108, the boot being stationary relative to both the camera body 104 and the prism 106. This mechanism allows for adjustment of the focus without removal of either the prism or the boot from the camera body.

Alternatively, the lens-holding element 109 defines a simple lug (not shown) secured thereto for rotation therewith, the lug projecting outwardly of boot 102 via a circumferential slot through the cylindrical wall of boot 102. The lug acts as a focus adjustment mechanism 120 by enabling the lens 108 to be manually rotated thereby and therewith, within the boot 102 relative to the camera body 104, from outside boot 102.

Operation

The operation of the apparatus of this invention will now be described with reference to all of the drawings.

The device is secured to the operator's head 10 by placing the head band 28 around the back of the head. The goggles 12 rest on the facial prominences and forehead. As is evident in FIG. 1 the camera 18 and prism 14 are positioned at the superior aspect of the goggles 12. This positioning allows for alignment of the prism 14 with the vocal cords 84 when the laryngoscopist has bent down towards the patient and extended her head as in FIG. 2. When not in this position, such as before laryngoscopy, the camera 18 and the prism 14 do not obscure the view through the goggles 12 towards the patient (See FIG. 1). The pentaprism 14 reflects light rays coming into the prism face 16 through a 90 degree angle by two reflections towards the camera 18. The camera thereby views the image in the same orientation as the operator. It is upright and right-left correct. The camera 18 and the prism 14 function as a single unit because they are wrapped tightly in heat shrink tubing 20.

Prior to the performance of direct laryngoscopy and intubation the operator needs to quickly verify the camera's view in relation to her own line of sight. To align the line of sight of the operator with the prism face 16 the operator holds out her thumb in front of the prism face 16 and notices on the video monitor 38 where her thumb appears on the screen. She manipulates the position of her thumbnail so that it appears in the vertical and horizontal center of the screen.

Minor horizontal adjustments can be made with slight rotational movement of the head. More extensive horizontal adjustments if needed are made by moving the camera 18 and prism 14 along the horizontal adjustment track 26 prior to the procedure. Minor vertical adjustments are made by slight changes in the degree of head tilt. Additional minor vertical adjustments can be made by pivoting the camera mount connection 24 on the angle adjustment mechanism 48. Further vertical adjustments can be made by moving the camera 18 up or down within the camera band 22. Similar to adjustment of the angle adjustment mechanism 48 this is accomplished by loosening of the wing nut 90. Loosening of the camera band 22 allows for either rotational manipulation or vertical movement of the camera 18 in relation to the goggles 12. Since the prism face is slightly lateral to the right eye the prism face 16 and camera 18 are slightly inwardly rotated from normal. This allows the camera's perspective to converge with the operator's monocular perspective at the appropriate working distance of approximately 10 to 14 inches.

Normally, vertical adjustment requiring movement of the camera 18 and prism 14 within the camera band 22 is not required. Intraoperator variability can be managed with small changes in head position and use of the colored alignment bands 46. Looking through her right eye 42 she can see the colored alignment bands 46 alongside the prism body 14 as shown in FIG. 5. By noting where her thumbnail is in relation to the different color bands 46 she can determine which color band is aligned next to her thumbnail when her thumbnail is at the vertical center of the screen. During the procedure she recreates the relationship of the colored alignment bands 46 to the target, now sighting the vocal cords 84 and glottic opening 86 instead of her thumbnail (see FIG. 5).

Colored alignment bands 46 are used because the proximity of the prism 14 to the operator's eye. This distance which is only a few centimeters is too short for the eye to clearly focus upon. The colored alignment bands 46 serve as an easily recognizable and distinctive means of aligning the prism face 16 between the right eye 42 and target.

When the operator has made the proper alignment and is performing laryngoscopy (as shown in FIG. 2 and 5) the prism face 16 is positioned a few millimeters lateral to the operator's right eye as shown in FIG. 3. There is no vertical discrepancy between the image received by the camera and the operator's right eye. Horizontally, the discrepancy between the right eye and the center of the prism face 16 is approximately a half centimeter. Because the tongue has been moved towards the left side of the mouth with the flange of the laryngoscope blade as shown in FIG. 5, there is some room along the right side of the mouth to see down to the vocal cords. There is sufficient space for the operator's right eye to directly view the vocal cords while the prism face 16 and therefore the camera 18 are imaging the same target. This allows other persons in the room to follow on the monitor what the laryngoscopist sees. Other persons in the room can visualize the passing of the endotracheal tube into the glottic opening.

Once the procedure is accomplished the operator assumes an erect posture above the patient as noted in FIG. 1. The various tasks that must be accomplished immediately following intubation, such as a rapid physical examination of the lungs, connecting the endotracheal tube to the ventilator, and checking several monitors are done with the goggles 12 still in place. Because of the relative superior positioning and small size of the camera 18 and the prism 14 on the goggles 12 the device does not impair the operator's ability to look downwards at the patient or about at the monitors. Once these urgent items are taken care of the operator can remove the device in a leisurely manner.

Summary, Ramifications, and Scope

Accordingly, the reader will see that the invention overcomes the visual restrictions inherent to imaging direct laryngoscopy and intubation. Prior art has been designed for imaging surgery and other applications distinctly different than laryngoscopy. Further advantages of the invention are that:

the camera's perspective is virtually aligned vertically and horizontally with the line of sight from the operator's right eye;

the alignment of the camera's perspective is accomplished through minor changes in head position and reference to alignment markers alongside the prism;

it does not interfere with direct laryngoscopy and intubation or any procedures occurring around intubation;

the operator can ensure that the camera will visualize the area of interest without having to look away from the target towards the video monitor;

it can be used by different operators with minimal training and with minimal adjustment between operators;

it is capable of obtaining high quality video images using standard laryngoscopy equipment without supplemental light sources;

it incorporates a pair of protective goggles that shield the operator's eyes from exposure to potential contact with the patient's body fluids; and it does not enter the oral cavity or touch the patient so it does not require sterilization between patients.

It is to be understood that while certain forms of this invention have been illustrated and described, it is not to be limited to the specific form or arrangement of parts described and shown.

Thus the scope of the invention should be determined by the appended claims and their legal equivalents, rather than by the examples given.

I claim:

1. A video apparatus adapted for imaging medical procedure of direct laryngoscopy and endotracheal intubation comprising:

a goggle mounted video camera, a means for substantially aligning the video camera's perspective with a monocular line of sight from an operator's dominant eye to a work area of the medical procedure of direct laryngoscopy and endotracheal intubation, wherein said aligning means permits alignment of the video camera's perspective with the monocular line of sight in a horizontal alignment exact within ±0.5 cm and a substantially exact vertical alignment, a reflecting means for transmitting an image of the work site to the operator's dominant eye and also reflecting the same image of the work site to the video camera, wherein the reflecting means comprises a five sided prism that reflects the image from the work site ninety degrees through two reflections or a beam splitting cube prism, wherein the camera's perspective is substantially aligned with the line of sight of the operator's dominant eye through slight changes in the operator's head position and with the reflecting means located alongside the alignment means, and a means for displaying the image from the video camera on a video monitor.

2. A video apparatus as in claim 1 wherein the reflecting means is positioned laterally adjacent to the line of sight from the dominant eye of the operator to the work area.

3. A video apparatus as in claim 1 wherein the reflecting means is attached to the goggles with a horizontal adjustment means.

4. A video apparatus as in claim 1 wherein the reflecting means is attached to the goggles with a vertical adjustment means.

5. A video apparatus as in claim 1 wherein the reflecting means is attached to the goggles with a rotational adjustment means.

6. A video apparatus as in claim 1 wherein the reflecting means is attached to an angle adjustment means.

7. A video apparatus as in claim 1 that is aligned with a high intensity light source directed at the camera's field of view.

8. The video apparatus of claim 1 including, intermediate said video camera and the video monitor, a video mirror device for corrective left-right flipping of the image.

9. The video apparatus of claim 1 wherein said video camera includes a hollow boot non-rotatably secured thereto, said prism non-rotatably secured to and within said boot, a focal lens rotatably secured to and within said boot, and a focal adjustment mechanism extending into said boot from outside thereto, whereby the focal lens may be rotated from outside said boot by said adjustment mechanism to adjust the focal length thereof.

10. A video apparatus for imaging a medical procedure of direct laryngoscopy and endotracheal intubation comprising:

a head mounted video camera, a means for substantially aligning the video camera's perspective with a monocular line of sight from an operator's dominant eye to the work area of the medical procedure of direct laryngoscopy and endotracheal intubation, wherein said aligning means permits alignment of the video camera's perspective with the monocular line of sight in a horizontal alignment exact within ±0.5 cm and a substantially exact vertical alignment, a reflecting means for transmitting an image of the work site to the operator's dominant eye and also reflecting the same image of the work site to the video camera, wherein the reflecting means comprises a five sided prism that reflects the image from the work site ninety degrees through two reflections or a beam splitting cube prism, wherein the camera's perspective is substantially aligned with the line of sight of the operator's dominant eye through slight changes in the operator's head position and with the reflecting means located alongside the alignment means, and a means for displaying the image from the video camera on a video monitor.

11. The video apparatus of claim 10 including, intermediate said video camera and the video monitor, a video mirror device for corrective left-right flipping of the image.

12. A video apparatus adapted for imaging a medical procedure of direct laryngoscopy and endotracheal intubation comprising:

an operator mounted video camera, a means for substantially aligning the video camera's perspective with a line of sight from an operator's dominant eye to a monocular work area of the medical procedure of direct laryngoscopy and endotracheal intubation, wherein said aligning means permits alignment of the video camera's perspective with the monocular line of sight in a horizontal alignment exact within ±0.5 cm and a substantially exact vertical alignment, a reflecting means for transmitting an image of the work site to the operator's dominant eye and also reflecting the same image of the work site to the video camera, wherein the reflecting means comprises a five sided prism that reflects the image from the work site ninety degrees through two reflections or a beam splitting cube prism, wherein the camera's perspective is substantially aligned with the line of sight of the operator's dominant eye through slight changes in the operator's head position and with the reflecting means located alongside the alignment means, and a means for displaying an image from the video camera on a video monitor.

13. The video apparatus of claim 12 wherein said video camera includes a hollow boot non-rotatably secured thereto, said prism non-rotatably secured to and within said boot, a focal lens rotatably secured to and within said boot, and a focal adjustment mechanism extending into said boot from outside thereto, whereby the focal lens may be rotated from outside said boot by said adjustment mechanism to adjust the focal length thereof.

14. A video apparatus for imaging a medical procedure of direct laryngoscopy and endotracheal intubation comprising:

a head mounted video camera, a means for substantially aligning the video camera's perspective with a monocular line of sight from an operator's dominant eye to the work area of the medical procedure of direct laryngoscopy and endotracheal intubation, said aligning means permitting alignment of the video camera's perspective with the monocular line of sight in a horizontal alignment exact within ±0.5 cm and a substantially exact vertical alignment, a reflecting means for transmitting an image of the work site to the operator's dominant eye and also reflecting the same image of the work site to the video camera, wherein the reflecting means comprises a five-sided prism that reflects the image from the work site ninety degrees through two reflections or a beam splitting cube prism, wherein the camera's perspective is substantially aligned with the line of sight of the operator's dominant eye through slight changes in the operator's head position and with the reflecting means located alongside the alignment means, and a means for displaying the image from the video camera on a video monitor.

* * * * *